United States Patent
Lorenzo et al.

(10) Patent No.: US 9,808,255 B2
(45) Date of Patent: *Nov. 7, 2017

(54) EMBOLIC COIL DETACHMENT MECHANISM WITH FLEXIBLE DISTAL MEMBER, RESISTIVE ELECTRICAL HEATING ELEMENT AND SHAPE MEMORY POLYMER ELEMENT

(75) Inventors: Juan A. Lorenzo, Davie, FL (US); Kirk Johnson, Weston, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/436,376

(22) Filed: Mar. 30, 2012

(65) Prior Publication Data

US 2013/0261658 A1 Oct. 3, 2013

(51) Int. Cl.
*A61B 17/12* (2006.01)
*A61B 17/00* (2006.01)

(52) U.S. Cl.
CPC .... *A61B 17/1214* (2013.01); *A61B 2017/00867* (2013.01); *A61B 2017/00871* (2013.01); *A61B 2017/00951* (2013.01); *A61B 2017/1205* (2013.01); *A61B 2017/12054* (2013.01); *A61B 2017/12068* (2013.01); *A61B 2017/12077* (2013.01)

(58) Field of Classification Search
CPC ...... A61B 2017/12068; A61B 2017/12077; A61B 17/1214; A61B 2017/00871; A61B 2017/00951; A61B 2017/00867; A61B 2017/12054; A61B 2017/1205
See application file for complete search history.

(56) References Cited

U.S. PATENT DOCUMENTS

| 5,108,407 A | 4/1992 | Geremia |
| 5,578,074 A | 11/1996 | Mirigian |
| 5,911,737 A | 6/1999 | Lee et al. |

(Continued)

FOREIGN PATENT DOCUMENTS

| CN | 101415459 A | 4/2009 |
| EP | 2644133 B1 | 5/2015 |

(Continued)

OTHER PUBLICATIONS

EPO, European Search Report from European Patent Application No. EP13162035 dated Jul. 24, 2013.
Japanese Office Action JP2013-068437, dated Feb. 7, 2017.

*Primary Examiner* — Katherine M Shi
*Assistant Examiner* — Michael Mendoza

(57) ABSTRACT

An embolic coil detachment system includes an elongated, flexible shape memory polymer tube having an inner wall surface defining an interior lumen. A distal portion of the shape memory polymer tube has an enlarged and reduced diameter configurations. An embolic coil is releasably mounted to the shape memory polymer tube by a headpiece releasably attached within a distal portion of the shape memory polymer tube. A resistive heating element disposed longitudinally along and in immediate contact with the inner wall surface of the distal tubular wall of the shape memory polymer tube provides direct, even heating to release the headpiece and embolic coil attached thereto when the resistive heating element is energized.

20 Claims, 6 Drawing Sheets

(56) References Cited

U.S. PATENT DOCUMENTS

| | | |
|---|---|---|
| 5,989,242 A | 11/1999 | Saadat et al. |
| 6,059,815 A | 5/2000 | Lee et al. |
| 6,102,917 A * | 8/2000 | Maitland et al. ............. 606/108 |
| 6,102,933 A | 8/2000 | Lee et al. |
| 6,277,125 B1 | 8/2001 | Barry |
| 6,575,965 B1 * | 6/2003 | Fitch et al. .................... 606/15 |
| 6,743,236 B2 | 6/2004 | Barry et al. |
| 7,578,826 B2 | 8/2009 | Gandhi et al. |
| 7,582,101 B2 | 9/2009 | Jones et al. |
| 7,591,833 B2 | 9/2009 | Jones et al. |
| 7,744,604 B2 | 6/2010 | Maitland et al. |
| 7,776,054 B2 | 8/2010 | Gandhi et al. |
| 7,780,680 B2 | 8/2010 | Gandhi et al. |
| 7,972,342 B2 | 7/2011 | Gandhi et al. |
| 2003/0069539 A1 * | 4/2003 | Gandhi et al. ............... 604/113 |
| 2006/0025801 A1 | 2/2006 | Lulo et al. |

FOREIGN PATENT DOCUMENTS

| | | |
|---|---|---|
| JP | 2002017736 A | 1/2002 |
| JP | 2003521992 A | 7/2003 |
| JP | 2005512674 A | 5/2005 |
| WO | WO 9701368 A1 | 1/1997 |
| WO | WO 0158366 A1 | 8/2001 |

* cited by examiner

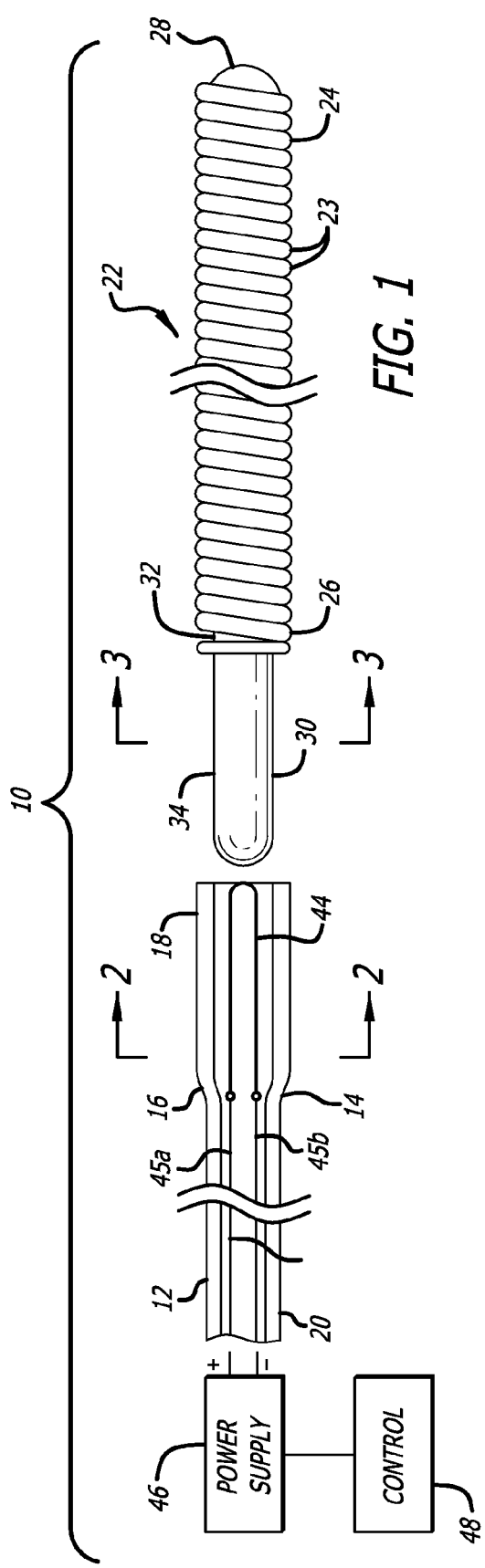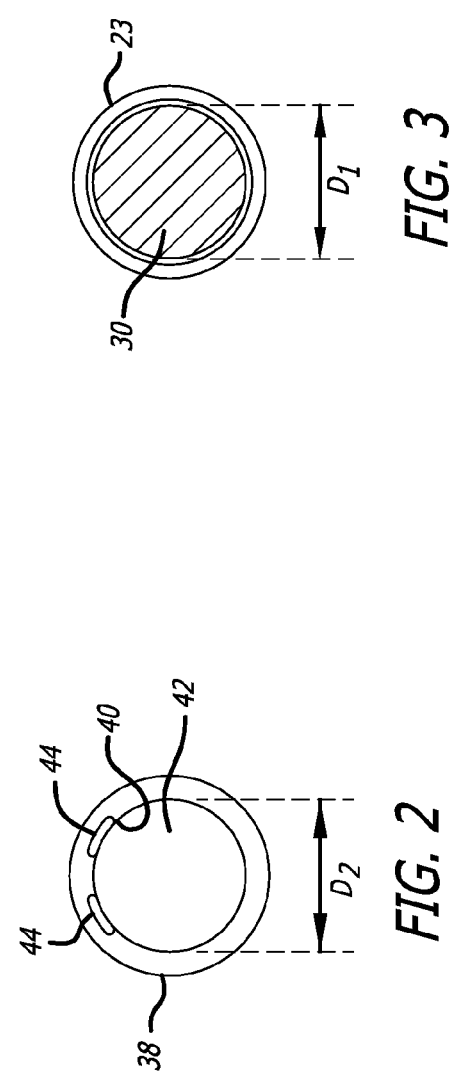

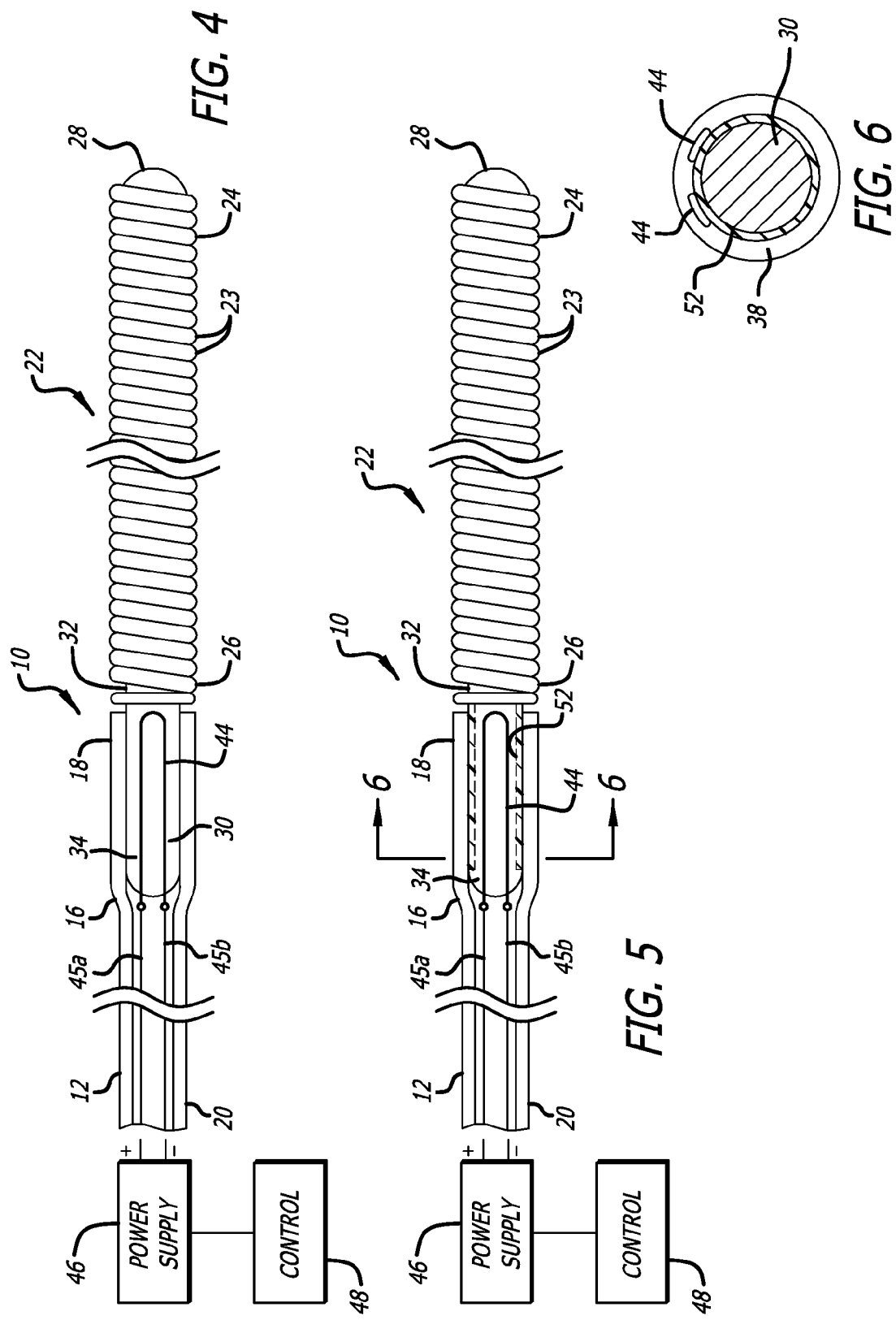

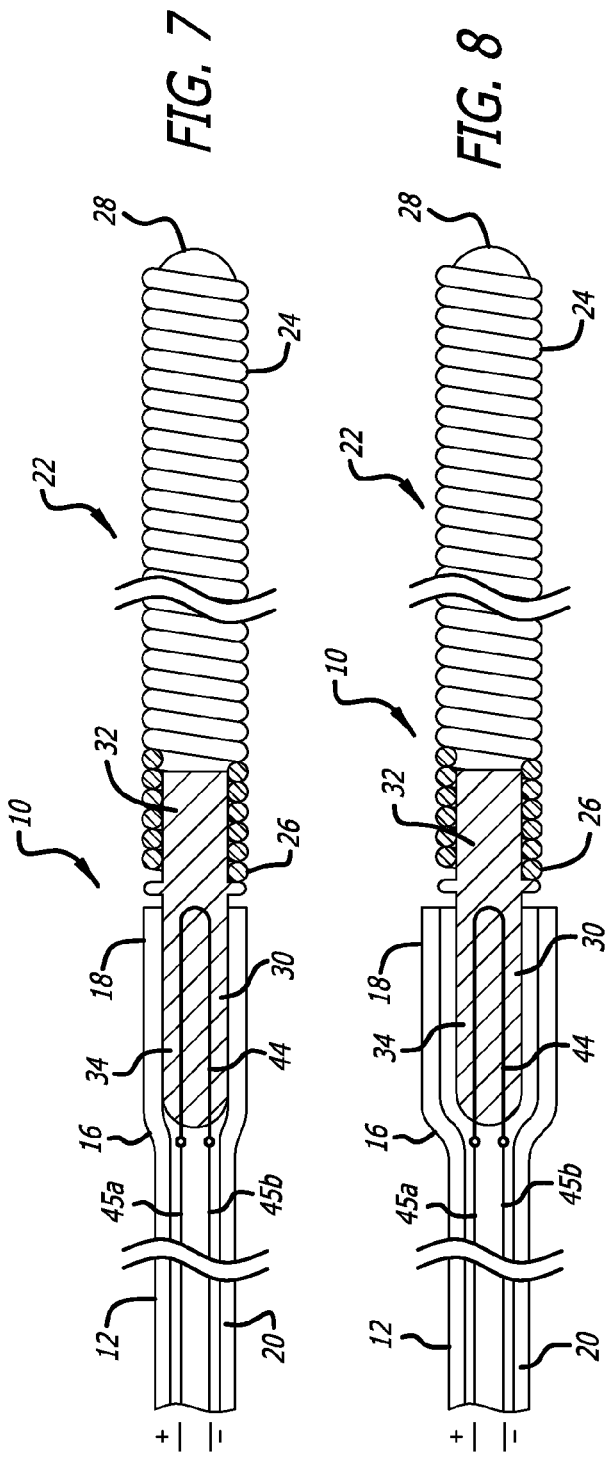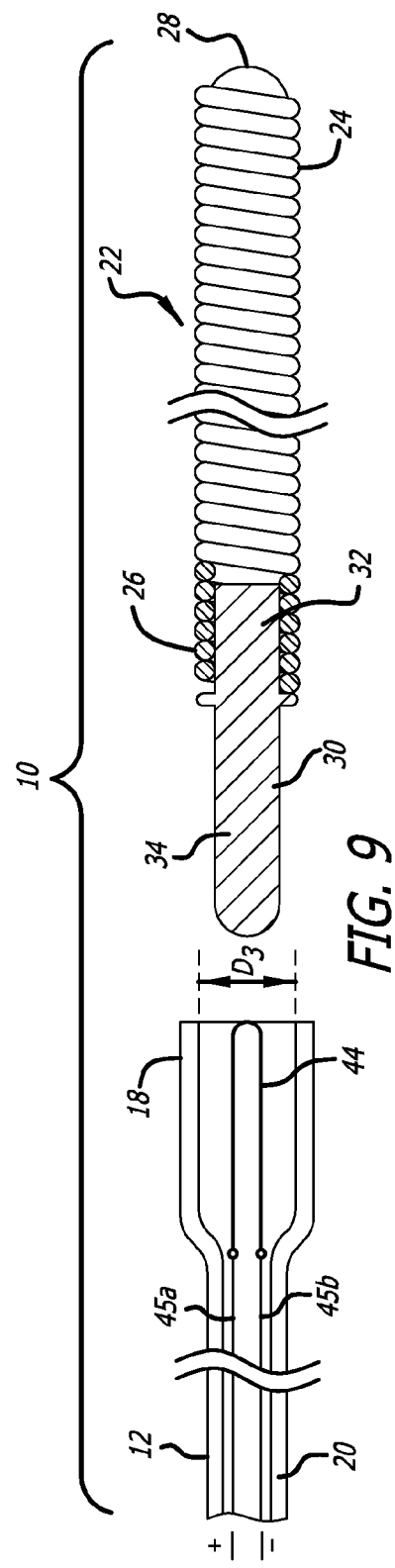

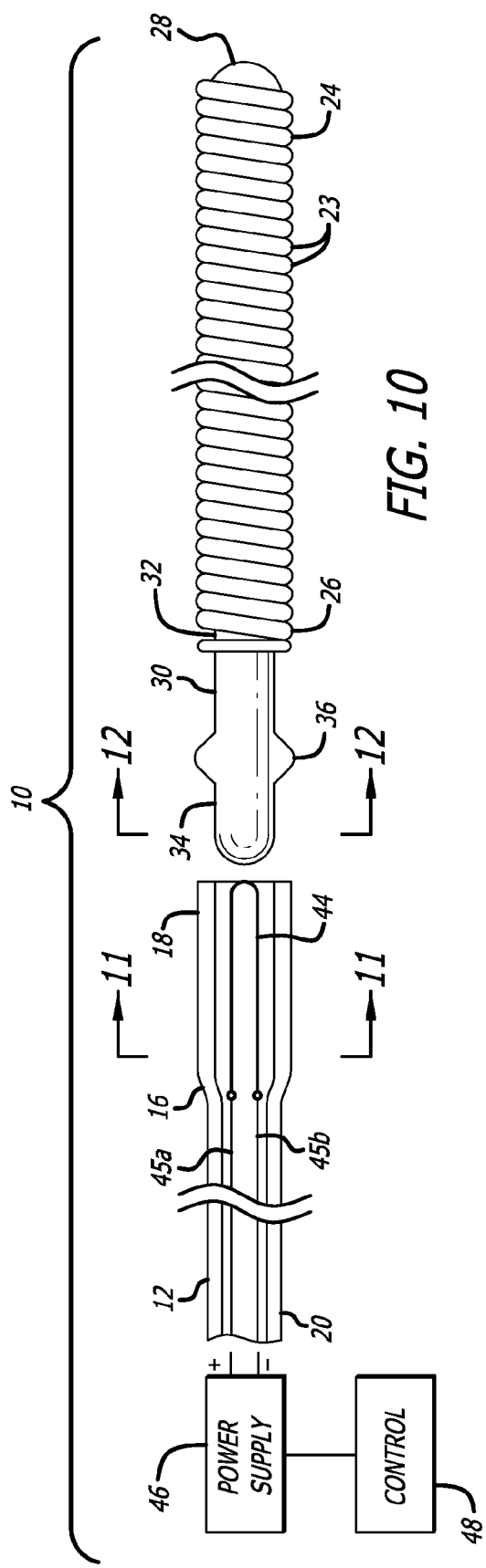
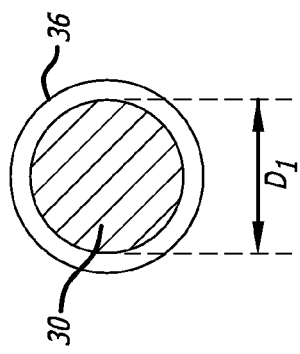
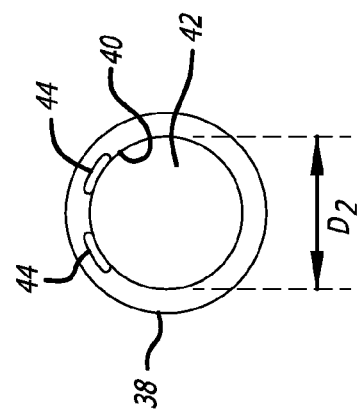

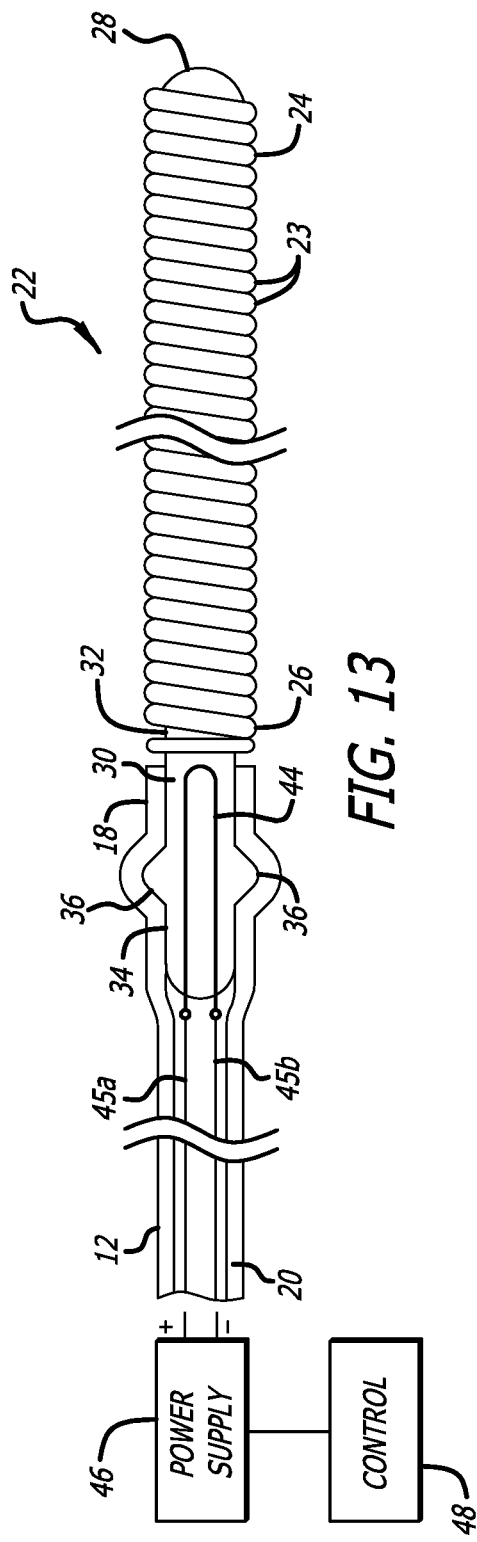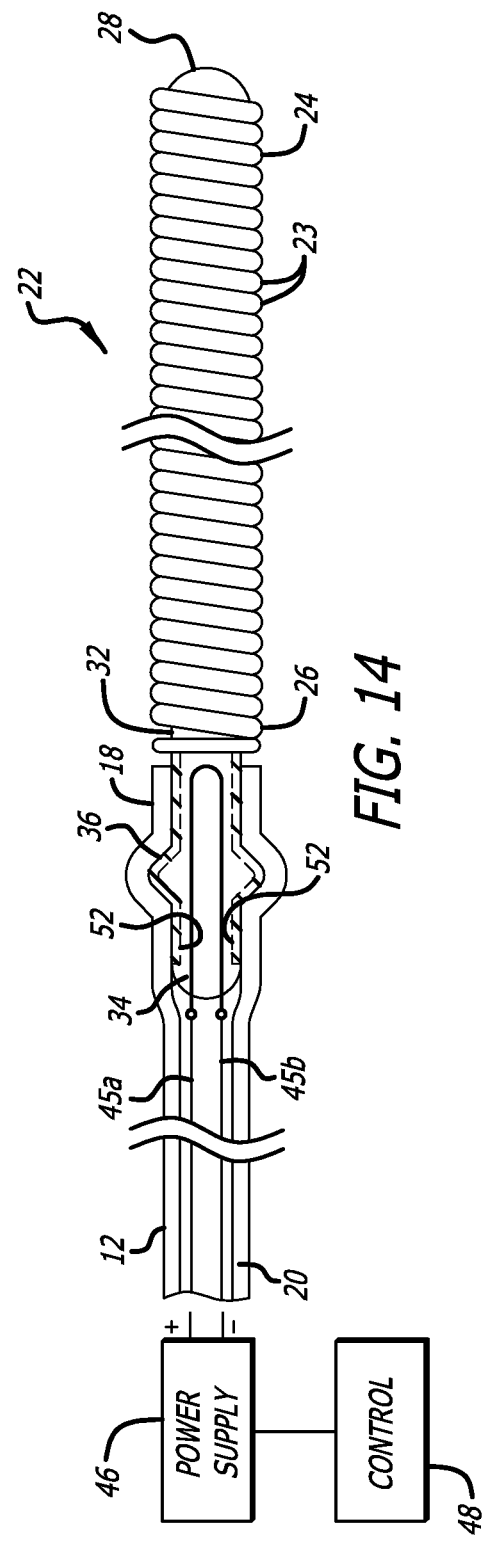

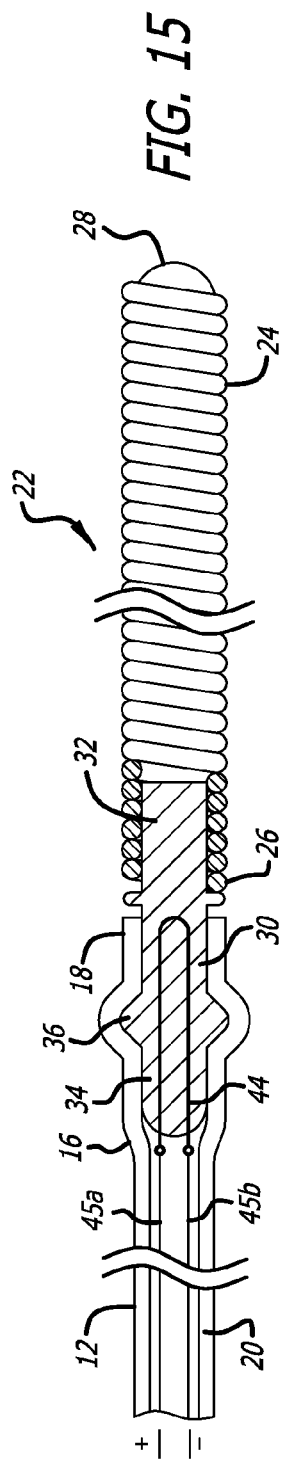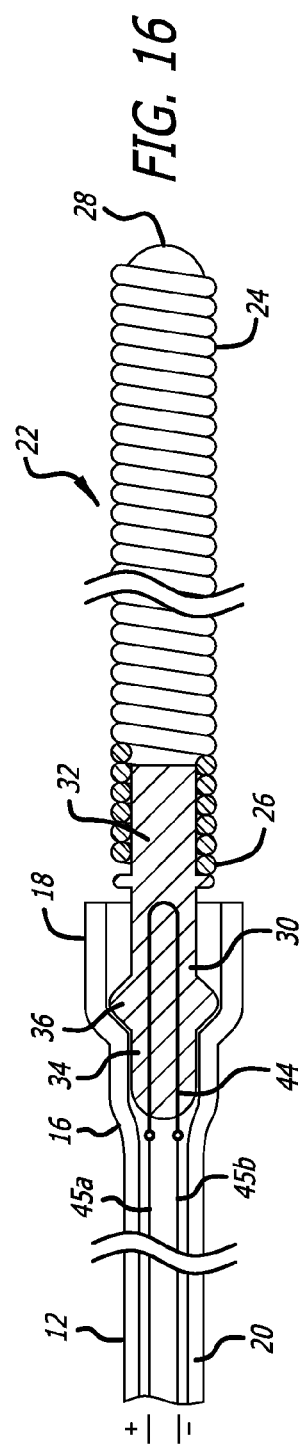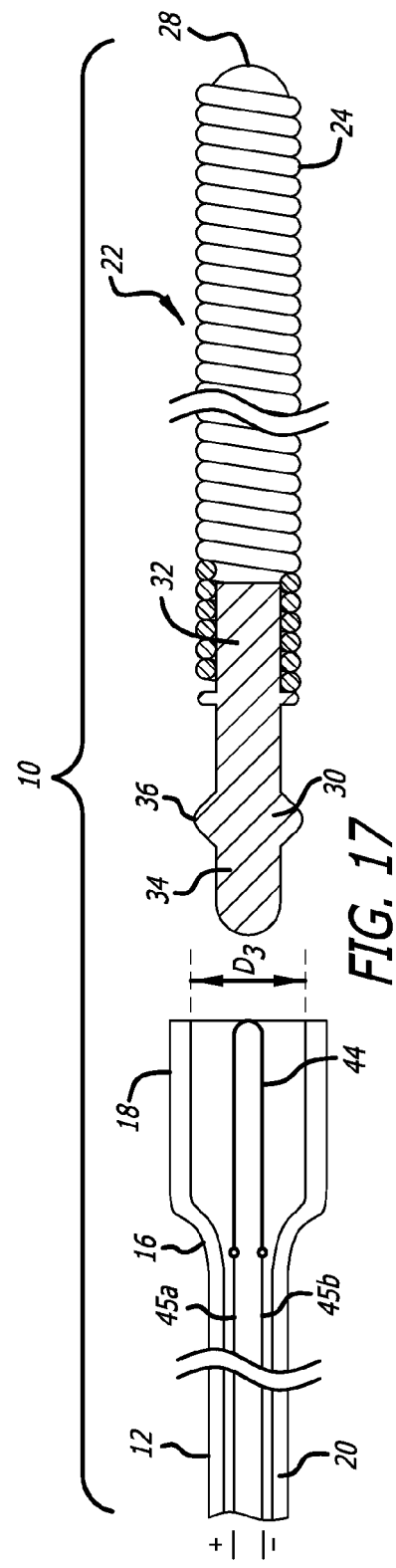

EMBOLIC COIL DETACHMENT MECHANISM WITH FLEXIBLE DISTAL MEMBER, RESISTIVE ELECTRICAL HEATING ELEMENT AND SHAPE MEMORY POLYMER ELEMENT

BACKGROUND OF THE INVENTION

This invention relates generally to devices for interventional therapeutic treatment or vascular surgery for treatment of defects in the vasculature, and more particularly concerns a system and method for delivering an embolic coil to a treatment site in a vasculature of a patient, such as for treatment of aneurysms.

Aneurysms have been treated with external surgically placed clips, detachable vasoocclusive balloons and embolus generating vasoocclusive devices such as one or more vasoocclusive coils, which are typically either placed within a blood vessel to block the flow of blood through a vessel making up that portion of the vasculature through the formation of an embolus, or are placed within an aneurysm stemming from the vessel to form such an embolus within the aneurysm. Delivery of one or more of such vasoocclusive coils has typically been accomplished by pushing them through a catheter to the target site.

In one conventional technique, a conductive guidewire delivers a high frequency current through the guidewire to melt and sever a joint to detach an implanted device from the guidewire. The patient is grounded during the procedure, and current is introduced via the guidewire, rather than with a two way current path.

Another device is known in which a device to be implanted is detached by application of a high-frequency current which melts and severs a resin that is used to retain the device to be implanted until the device is to be deployed. In another known device, an electrolytically severable link is dissolved by activation of a power source electrically coupled to the electrolytically severable link to detach the device to be implanted.

An apparatus for deployment of a micro-coil is also known in which the micro-coil is detachably mounted to the distal portion of a pusher by a tubular collar that can be heated by an electrical resistance coil to expand the collar and release and deploy the therapeutic device.

Such devices that release the interventional device by melting or dissolving the intermediate section between the catheter tip and implanted device may cause thermal damage of surrounding tissues during detachment that can cause embolization in the bloodstream, and may also potentially release undesirable particles of materials into the bloodstream that can also cause embolization in the bloodstream.

In order to allow delivery and withdrawal of such embolic coils, one known implant delivery assembly utilizes a shape memory decoupling mechanism activated when exposed to body temperature. A cooling solution is flushed through the catheter during introduction and placement of the implant in order to prevent premature release of the implant prior to the time that the implant is to be released. Another implant delivery assembly includes an electrical heating system for heating the coupling mechanism to a temperature at which the shape memory material returns to its original shape, to deploy the implant.

A thermally activated occlusive implant delivery system is also known in which a pusher includes a distal coupling formed of shape memory material having different configurations dependent upon temperature, that interlocks with the implant in one configuration and that releases the implant in another configuration.

In another device for releasing an embolic coil inside an aneurysm, a coupling made of a shape memory alloy is responsive to a change in temperature beyond a predetermined transformation point so as to change the shape of the coupling from a first configuration, in which the coupling receives and holds the proximal end of the coil, to a second configuration in which the coil can be released from the coupling. An energy receiver is used to heat the coupling to a temperature above the transformation point with laser or electrical energy received from an external source.

There is a need for an improved apparatus for deploying therapeutic interventional devices with a strategically placed heating element that provides direct, even heating of a flexible shape memory polymer coupling releasably retaining an embolic coil for delivery when the heating element is energized, without causing thermal damage to surrounding tissues, and without releasing undesirable particles of materials into the bloodstream and risking the formation of emboli in the bloodstream. The present invention meets these and other needs.

SUMMARY OF THE INVENTION

Briefly and in general terms, the present invention provides for a detachment system and method for delivering an embolic coil to a treatment site in a vasculature of a patient, utilizing a resistive heating element contained within an interior lumen of a distal portion of a flexible shape memory polymer tube, and disposed longitudinally along and in immediate contact with an inner wall surface of the tubular wall of the distal portion of the flexible shape memory polymer tube, to provide direct, even heating of at least a substantial majority of the length of the distal portion of the flexible shape memory polymer tube when the resistive heating element is energized.

The present invention accordingly provides for a detachment system and method for delivering an embolic coil to a treatment site in a vasculature of a patient, including an elongated, flexible shape memory polymer tube having a longitudinal axis, a distal portion and a proximal portion. The elongated, flexible shape memory polymer tube has a tubular wall with an inner wall surface defining an interior lumen extending through the elongated, flexible shape memory polymer tube between the distal portion and the proximal portion of the elongated, flexible shape memory polymer tube. In a presently preferred aspect, the distal portion of the elongated, flexible shape memory polymer tube has an enlarged diameter configuration with a permanent shape and reduced diameter configuration with a temporary shape. The enlarged diameter configuration of the distal portion of the elongated, flexible shape memory polymer tube preferably has an enlarged diameter with an inner diameter that is larger than an outer diameter of the headpiece.

A therapeutic embolic coil is releasably mounted to the distal portion of the elongated, flexible shape memory polymer tube by a headpiece having a distal portion attached to a proximal end of the embolic coil. The proximal portion of the headpiece is advantageously releasably attached within the distal portion of the elongated, flexible shape memory polymer tube in the configuration with a temporary shape. In a presently preferred aspect, the therapeutic embolic coil is a helical embolic coil.

A resistive heating element is advantageously contained within the interior lumen of the distal portion of the flexible shape memory polymer tube, and is disposed longitudinally along and in immediate contact with the inner wall surface of the tubular wall of the distal portion of the flexible shape memory polymer tube, to provide direct, even heating of at least a substantial majority of the length of the distal portion of the flexible shape memory polymer tube when the resistive heating element is energized. The proximal portion of the headpiece and the embolic coil attached thereto are releasable from the distal portion of said elongated, flexible shape memory polymer tube by heating of the distal portion of the elongated, flexible shape memory polymer tube to cause the distal portion of the elongated, flexible shape memory polymer tube to change from the temporary shape having a reduced diameter configuration to said enlarged diameter configuration.

In a presently preferred aspect, two electrical conductors extend through the interior lumen of the elongated, flexible shape memory polymer tube and are electrically connected to the resistive heating element for powering the resistive heating element to heat the distal portion of the elongated, flexible shape memory polymer tube. In another presently preferred aspect, the proximal portion of the headpiece has a generally cylindrical configuration, and the proximal portion of the headpiece extends proximally of the proximal portion of the embolic coil. In another presently preferred aspect, the proximal portion of the headpiece may include at least one surface feature, which is preferably a generally cylindrical enlarged portion, and may be smoothly rounded, for example.

In another presently preferred aspect, the reduced diameter configuration of the temporary shape of the distal portion of the elongated, flexible shape memory polymer tube has an inner diameter smaller than the outer diameter of the headpiece. In another presently preferred aspect, the headpiece and the distal portion of the elongated, flexible shape memory polymer tube are releasably joined together by an adhesive placed between the headpiece and the distal portion of the elongated, flexible shape memory polymer tube.

These and other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1 is a partial sectional schematic diagram of a pusher member and embolic coil of the detachment system of the present invention.

FIG. 2 is a cross-sectional view of the distal portion of the pusher member of the detachment system taken along line 2-2 of FIG. 1.

FIG. 3 is a cross-sectional view of the headpiece of the embolic coil of the detachment system taken along line 3-3 of FIG. 1.

FIG. 4 is a partial sectional schematic diagram of the pusher member and embolic coil of the detachment system of FIG. 1 joined together.

FIG. 5 is a partial sectional schematic diagram similar to FIG. 4 showing a variation of detachment system including adhesive additionally joining the pusher member and embolic coil of the detachment system of FIG. 1 together.

FIG. 6 is a cross-sectional view taken along line 6-6 of FIG. 5.

FIG. 7 is a partial sectional schematic diagram of the pusher member and embolic coil of the detachment system of FIG. 1 joined together, prior to activation of the resistive heating element.

FIG. 8 is a partial sectional schematic diagram similar to FIG. 7, illustrating activation of the resistive heating element to change the distal portion of the flexible shape memory polymer tube to its enlarged diameter permanent shape.

FIG. 9 is a partial sectional schematic diagram similar to FIG. 7, illustrating release of the headpiece and embolic coil.

FIG. 10 is a partial sectional schematic diagram of a variation of the detachment system of FIG. 1 including a surface feature on the headpiece of the embolic coil.

FIG. 11 is a cross-sectional view of the distal portion of the pusher member of the detachment system taken along line 11-11 of FIG. 10.

FIG. 12 is a cross-sectional view of the headpiece of the embolic coil of the detachment system taken along line 12-12 of FIG. 10.

FIG. 13 is a partial sectional schematic diagram of the pusher member and embolic coil of the detachment system of FIG. 10 joined together.

FIG. 14 is a partial sectional schematic diagram similar to FIG. 13 showing a variation of detachment system including adhesive additionally joining the pusher member and embolic coil of the detachment system of FIG. 10 together.

FIG. 15 is a partial sectional schematic diagram of the pusher member and embolic coil of the detachment system of FIG. 10 joined together, prior to activation of the resistive heating element.

FIG. 16 is a partial sectional schematic diagram similar to FIG. 15, illustrating activation of the resistive heating element to change the distal portion of the flexible shape memory polymer tube to its enlarged diameter permanent shape.

FIG. 17 is a partial sectional schematic diagram similar to FIG. 15, illustrating release of the headpiece and embolic coil.

DETAILED DESCRIPTION OF THE PREFERRED EMBODIMENTS

Referring to the drawings, which are provided by way of example, and not by way of limitation, the present invention provides for a detachment system 10 for delivering embolic coils to a treatment site in a vasculature of a patient. The detachment system includes an elongated, flexible pusher member 12 having a distal portion 14 formed from a flexible shape memory polymer tube 16 having a distal portion 18, and a proximal portion 20, for release and deployment of a therapeutic embolic coil 22, which in one presently preferred aspect includes helical coils 23. The therapeutic embolic coil typically has a distal end 24 and a proximal end 26, and typically includes a rounded distal tip 28 attached to the distal end of the embolic coil, such as by solder, welding or adhesive, for example. The therapeutic embolic coil also preferably includes a headpiece or stem 30 having a distal portion 32 and a proximal portion 34. The therapeutic embolic coil is typically released within the vasculature of a patient, introduced through a delivery catheter (not shown), for treatment of a portion of a patient's vasculature, such as an aneurysm.

In one presently preferred aspect, the headpiece or stem has a generally cylindrical configuration. Referring to FIGS. 10 and 12-17, in another presently preferred aspect, the headpiece or stem may include one or more surface features 36, such as a generally cylindrical enlarged portion, which can be smoothly rounded, as is illustrated in FIG. 10, or which may be grooved, sharply edged or squared, or of any other similar suitable shape, for example, in order to increase the strength of the attachment of the headpiece or stem to the distal portion of the flexible shape memory polymer tube prior to activating the resistive heating element to heat the distal portion of the flexible shape memory polymer tube to change the shape of the distal portion of the flexible shape memory polymer tube to its enlarged diameter permanent shape, as will be further explained below. The distal portion of the headpiece or stem is typically attached to the proximal end of the embolic coil, such as by solder, welding or adhesive, for example, leaving the proximal portion of the headpiece or stem extending proximally of the proximal portion of the embolic coil.

Referring to FIGS. 1, 2, 10 and 11, the flexible shape memory polymer tube has a tubular wall 38 having an inner wall surface 40 defining an interior lumen 42 extending through the elongated, flexible shape memory polymer tube between the distal and proximal portions of the flexible shape memory polymer tube. The flexible shape memory polymer tube is preferably formed of a shape memory polymer having a glass transition temperature (Tg) above body temperature, such as polyurethane, for example, that can be heat treated to have shape memory behavior, although the flexible shape memory polymer tube may also be formed from other suitable shape memory materials, such as a shape memory metal, such as a nickel titanium alloy, for example, that can be heat treated to have shape memory behavior.

A resistive heating element 44 advantageously is contained within the interior lumen of the distal portion of the flexible shape memory polymer tube, and is disposed longitudinally along and in immediate contact with the inner wall surface of the tubular wall of the distal portion of the flexible shape memory polymer tube, to provide direct, even heating of at least a substantial majority of the length of the distal portion of the flexible shape memory polymer tube when the resistive heating element is energized.

Two electrical conductors 45a, 45b extend through the interior lumen of the flexible shape memory polymer tube from a proximal portion of the flexible shape memory polymer tube to the resistive heating element, and are operatively electrically connected between the resistive heating element and a power supply 46, which can in turn be operated by a control unit 48. Alternatively, the power supply and control unit may optionally be combined.

The resistive heating element can be fabricated from platinum, stainless steel, or other high resistance materials, and the electrical connectors can be copper or other highly electrically conductive leads, for example. The power supply can be operated to supply electrical current to the resistive heating element to heat the distal portion of the flexible shape memory polymer tube to cause the distal portion of the flexible shape memory polymer tube to expand and release the therapeutic helical embolic coil, as is illustrated in FIGS. 7-9. The lumen of the flexible shape memory polymer tube advantageously insulates the heating of the flexible shape memory polymer tube to avoid thermal damage to surrounding tissues during heating of the flexible shape memory polymer tube to deploy the therapeutic helical embolic coil.

Referring to FIGS. 1 and 10, the therapeutic helical embolic coil is releasably mounted to the distal portion of the flexible shape memory polymer tube by inserting the proximal portion of the headpiece or stem into the distal portion of the flexible shape memory polymer tube, with the resistive heating element disposed between the inner wall surface of the tubular wall of the distal portion of the flexible shape memory polymer tube and the proximal portion of the headpiece or stem. Referring to FIGS. 2, 3, 11 and 12, the embolic coil headpiece or stem preferably has an outer diameter $D_1$ larger than an inner diameter $D_2$ of the lumen at the distal portion of the flexible shape memory polymer tubing, thus creating an interference fit between the embolic coil headpiece or stem and the distal portion of the flexible polymer tubing inner diameter. This dimensional interference prevents the premature separation between the embolic coil and the tube and the outer diameter of the embolic coil headpiece.

The distal portion of the flexible shape memory polymer tube preferably has a permanent shape with an enlarged diameter configuration illustrated in FIGS. 9 and 17 having a larger inner diameter $D_3$ than the outer diameter $D_1$ of the headpiece or stem. This permanent shape of the distal portion of the flexible shape memory polymer tube is changed into a temporary shape having a reduced diameter configuration with an inner diameter smaller than the outer diameter of the headpiece or stem by heating and deforming the distal portion of the flexible shape memory polymer tube so as to reduce the inner diameter of the distal portion of the flexible shape memory polymer tube to be smaller than the outer diameter of the embolic coil headpiece or stem.

Alternatively, the headpiece or stem can be inserted into the distal portion of the flexible shape memory polymer tube while the distal portion of the flexible shape memory polymer tube has a permanent shape with an enlarged diameter configuration with a larger inner diameter than the outer diameter of the headpiece or stem, with the resistive heating element disposed between the inner wall surface of the tubular wall of the distal portion of the flexible shape memory polymer tube and the proximal portion of the headpiece or stem, and then subsequently the distal portion of the flexible shape memory polymer tube can be heated and deformed so as to reduce the inner diameter of the distal portion of the flexible shape memory polymer tube to be smaller than the outer diameter of the embolic coil headpiece or stem, such that the flexible shape memory polymer tube grabs onto the headpiece or stem, and then cooling the distal portion of the flexible shape memory polymer tube to set the distal portion of the flexible shape memory polymer tube in place over the headpiece or stem.

In another preferred variation illustrated in FIGS. 5, 6 and 14, an adhesive 52, such as cyanoacrylate adhesive or epoxy, for example, may be placed at the interface of the headpiece or stem with the distal portion of the flexible shape memory polymer tube and/or one or more surface features in order to increase the strength of the attachment of the headpiece or stem to the distal portion of the flexible shape memory polymer tube prior to activating the resistive heating element to change the distal portion of the flexible shape memory polymer tube to its enlarged diameter permanent shape.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A detachment system for delivering embolic coils to a treatment site in a vasculature of a patient, comprising:
   an elongated, flexible shape memory polymer tube having a longitudinal axis, a distal portion and a proximal portion, said elongated, flexible shape memory polymer tube having a tubular wall with an inner wall surface defining an interior lumen extending through the elongated, flexible shape memory polymer tube between the distal portion and the proximal portion of the elongated, flexible shape memory polymer tube, the distal portion of the elongated, flexible shape memory polymer tube having a permanent shape and a temporary shape;

a therapeutic embolic coil releasably mounted to the distal portion of said elongated, flexible shape memory polymer tube, said embolic coil having a distal end and a proximal end;

a headpiece having a distal portion and a proximal portion, the distal portion of the headpiece being attached to the proximal end of the embolic coil, and the proximal portion of the headpiece being releasably attached within said distal portion of said elongated, flexible shape memory polymer tube, said permanent shape having an enlarged diameter configuration with an inner diameter that is larger than an outer diameter of the headpiece; and a resistive heating element contained within the interior lumen of the distal portion of the flexible shape memory polymer tube, and disposed longitudinally along and in immediate contact with the inner wall surface of the tubular wall of the distal portion of the flexible shape memory polymer tube between the inner wall surface of said tubular wall of said elongated, flexible shape memory polymer tube and said proximal portion of said headpiece, and wherein said proximal portion of the headpiece is configured to be releasable from said distal portion of said elongated, flexible shape memory polymer tube by heating of said distal portion of the elongated, flexible shape memory polymer tube to cause said distal portion of the elongated, flexible shape memory polymer tube to change from said temporary shape having a reduced diameter configuration to said enlarged diameter configuration.

2. The detachment system of claim 1, further comprising two electrical conductors extending through the interior lumen of the elongated, flexible shape memory polymer tube and electrically connected to the resistive heating element.

3. The detachment system of claim 1, wherein said resistive heating element is disposed along a longitudinal axis of the distal portion of the elongated, flexible shape memory polymer tube.

4. The detachment system of claim 1, wherein said therapeutic embolic coil comprises a helical embolic coil.

5. The detachment system of claim 1, wherein said proximal portion of said headpiece has a generally cylindrical configuration.

6. The detachment system of claim 1, wherein said proximal portion of the headpiece extends proximally of said proximal portion of the embolic coil.

7. The detachment system of claim 1, wherein said proximal portion of said headpiece comprises at least one surface feature.

8. The detachment system of claim 7, wherein said at least one surface feature comprises a generally cylindrical enlarged portion.

9. The detachment system of claim 8, wherein said generally cylindrical enlarged portion is smoothly rounded.

10. The detachment system of claim 1, wherein said temporary shape has a reduced diameter configuration with an inner diameter smaller than the outer diameter of the headpiece.

11. The detachment system of claim 1, wherein said headpiece and the distal portion of the elongated, flexible shape memory polymer tube are releasably joined together by an adhesive placed between the headpiece and the distal portion of the elongated, flexible shape memory polymer tube.

12. A detachment system for delivering embolic coils to a treatment site in a vasculature of a patient, comprising:

an elongated, flexible shape memory polymer elongated, flexible shape memory polymer tube having a distal portion and a proximal portion, said elongated, flexible shape memory polymer tube having a tubular wall with an inner wall surface defining an interior lumen extending through the elongated, flexible shape memory polymer tube between the distal portion and the proximal portion of the elongated, flexible shape memory polymer tube, the distal portion of the elongated, flexible shape memory polymer tube having a temporary shape having a first configuration with a first inner diameter and a permanent shape having a second configuration with a second inner diameter that is larger than said first inner diameter of said first configuration of said temporary shape;

a headpiece having a distal portion and a proximal portion, said proximal portion of said headpiece being releasably mounted within said distal portion of said elongated, flexible shape memory polymer tube, said second inner diameter of said second configuration of said permanent shape of said elongated, flexible shape memory polymer tube being larger than an outer diameter of said headpiece;

a therapeutic embolic coil having a distal end and a proximal end, said proximal end of said therapeutic embolic coil being fixedly attached to the distal portion of said headpiece, said proximal portion of the headpiece extending proximally of said proximal portion of the embolic coil; and a resistive heating element contained within the interior lumen of the distal portion of the flexible shape memory polymer tube, and disposed longitudinally along and in immediate contact with the inner wall surface of the tubular wall of the distal portion of the flexible shape memory polymer tube between the inner wall surface of said tubular wall of said elongated, flexible shape memory polymer tube and said proximal portion of said headpiece, said resistive heating element being configured to provide direct, even heating of at least a substantial majority of the length of the distal portion of the flexible shape memory polymer tube when the resistive heating element is energized, whereby said headpiece and said therapeutic embolic coil attached thereto are configured to be releasable from said distal portion of said elongated, flexible shape memory polymer tube by heating of said distal portion of the elongated, flexible shape memory polymer tube by said resistive heating element to cause said distal portion of the elongated, flexible shape memory polymer tube to change from said temporary shape having a reduced diameter configuration to said enlarged diameter configuration.

13. The detachment system of claim 12, wherein said temporary shape of said distal portion of said elongated, flexible shape memory polymer tube has a reduced diameter configuration with an inner diameter smaller than the outer diameter of the headpiece.

14. The detachment system of claim 12, further comprising two electrical conductors extending through the interior lumen of the elongated, flexible shape memory polymer tube and electrically connected to the resistive heating element.

15. The detachment system of claim 12, wherein said therapeutic embolic coil comprises a helical embolic coil.

16. The detachment system of claim 12, wherein said proximal portion of said headpiece has a generally cylindrical configuration.

17. The detachment system of claim 12, wherein said proximal portion of said headpiece comprises at least one surface feature.

18. The detachment system of claim 17, wherein said at least one surface feature comprises a generally cylindrical enlarged portion.

19. The detachment system of claim 18, wherein said generally cylindrical enlarged portion is smoothly rounded.

20. The detachment system of claim 12, wherein said headpiece and the distal portion of the elongated, flexible shape memory polymer tube are releasably joined together by an adhesive placed between the headpiece and the distal portion of the elongated, flexible shape memory polymer tube.

* * * * *